US011572429B2

(12) United States Patent
Gallardo Ruiz et al.

(10) Patent No.: US 11,572,429 B2
(45) Date of Patent: Feb. 7, 2023

(54) HYDROGELS BASED ON VINYL-CAPROLACTAM

(71) Applicant: Consejo Superior de Investigaciones Científicas (CSIC), Madrid (ES)

(72) Inventors: Alberto Gallardo Ruiz, Madrid (ES); Juan Rodríguez Hernández, Madrid (ES); Helmut Reinecke, Madrid (ES); Carlos Elvira Pujalte, Madrid (ES); Carolina García Sánchez, Madrid (ES); Enríque Martínez Campos, Madrid (ES)

(73) Assignee: Consejo Superior De Investigaciones Científicas (CSIC)

( * ) Notice: Subject to any disclaimer, the term of this patent is extended or adjusted under 35 U.S.C. 154(b) by 0 days.

(21) Appl. No.: 17/064,183

(22) Filed: Oct. 6, 2020

(65) Prior Publication Data

US 2021/0017316 A1 Jan. 21, 2021

Related U.S. Application Data

(63) Continuation of application No. PCT/ES2019/070235, filed on Apr. 5, 2019.

(30) Foreign Application Priority Data

Apr. 6, 2018 (ES) ................................ ES201830348

(51) Int. Cl.

| | |
|---|---|
| ***C08F 2/46*** | (2006.01) |
| ***C08F 2/50*** | (2006.01) |
| ***C08G 61/04*** | (2006.01) |
| ***C08F 226/06*** | (2006.01) |
| ***C08F 26/06*** | (2006.01) |
| ***C08J 3/075*** | (2006.01) |
| ***C12N 5/00*** | (2006.01) |

(52) U.S. Cl.

CPC ............ *C08F 226/06* (2013.01); *C08F 26/06* (2013.01); *C08J 3/075* (2013.01); *C12N 5/0018* (2013.01); *C08J 2339/04* (2013.01); *C12N 2533/30* (2013.01)

(58) Field of Classification Search

CPC ..... C08J 3/075; C08J 2339/04; C12N 5/0068; C12N 5/0018; C12N 2537/10; C12N 2533/30; C08F 26/06; C08F 226/06; C08F 220/34; C08F 220/382; C08F 220/585; C08F 220/387; C08F 220/02; C08F 220/20; C08F 222/102; C08F 222/1025

USPC ........... 522/79, 74, 71, 189, 184, 6, 1; 520/1

See application file for complete search history.

(56) References Cited

U.S. PATENT DOCUMENTS

| | | | | |
|---|---|---|---|---|
| 4,436,887 | A * | 3/1984 | Chromecek | A61L 27/16 351/159.33 |
| 2009/0018233 | A1* | 1/2009 | Nunez | C08F 216/125 523/107 |
| 2010/0172990 | A1 | 7/2010 | Forcada Garcia | |
| 2019/0352443 | A1* | 11/2019 | Nunez | C08F 226/10 |
| 2020/0002494 | A1* | 1/2020 | Gallardo Ruiz | C08J 7/18 |
| 2020/0012015 | A1* | 1/2020 | Nunez | C08L 83/04 |

OTHER PUBLICATIONS

Bora Lee et al.; "Initiated chemical vapor deposition of thermoresponsive poly (N-vinylcaprolactam) thin films for cell sheet engineering"; Published in final edited form as: Acta Biomater: Aug. 2013; 9(8): 7698.doi:10.1016/j.actbio.2013.04.049—(21) pages.

Yang, Boguang; Wang, Changyong; Zhang, Yabin; Ye, Lei; Qian, Yufeng; Shu, Yao; Wang, Jinmei; Li, Junjie; Yao, Fanglian; "A thermoresponsive poly(N-vinylcaprolactam-co-sulfobetaine methacrylate) zwitterionic hydrogel exhibiting switchable anti-biofouling and cytocompatibility"; Polymer Chemistry, 2015; 6 (18): 3431-3442)—(12) pages.

Cakal, Elcin; Cavus, Selva; "Novel Poly(N-vinylcaprolactam-co-2-(diethylamino)ethyl methacrylate) Gels: Characterization and Detailed Investigation on Their Stimuli-Sensitive Behaviors and Network Structure"; Ind. Eng. Chem Res 2010, 49, 22, 11741-11751—(11) pages.

Bulmus, Volga; Chan, Yannie; Nguyen, Quyen; Tran, Hong L; "Synthesis and characterization of degradable polyhydroxymethacrylate microgels: use of acid-labile crosslinkers"; Macromolecular Bioscience (2007), 7 (4), 446-455; RSC Adv. 2014, 4, 35950-35958—(10) pages.

Lim et al.; "Cell Sheet Detachment from Poly(N-vinylcaprolactam-co-N-iso-propylacrylamide) Grafted onto Tissue Culture Polystyrene Dishes"; Journal of Industrial and Engineering Chemistry 2007, 13 (1), 21-26)—(6) pages.

European Supplementary Search Report dated Nov. 22, 2021; Application No. EP 19 78 2259—(3) pages.

Sala et al.; "Thermosensitive Poly (N-vinylcaprolactam) Injectable Hydrogels for Cartilage Tissue Engineering"; Tissue Engineering: Part A, vol. 23, Nos. 17 and 18, 2017; Online Publication Date Apr. 6, 2017—(11) pages.

* cited by examiner

*Primary Examiner* — Jessica Whiteley

(74) *Attorney, Agent, or Firm* — Boyle Fredrickson, SC

(57) ABSTRACT

The invention relates to a hydrogel based on vinyl caprolactam, with or without additional monomers, and at least two crosslinkers. The invention also relates to a method for obtaining said material and to the use thereof to culture cells/engineer cell monolayers, as well as supports for cell culture and transplant.

22 Claims, 5 Drawing Sheets

HYDROGELS BASED ON VINYL-CAPROLACTAM

CROSS-REFERENCE TO RELATED APPLICATIONS

This application is a continuation of and claims priority to PCT Application No. PCT/ES2019/070235, filed on Apr. 5, 2019, which, in turn, claims priority to Spanish Application No. P201830348, filed on Apr. 6, 2018. The entire contents of each of these applications is incorporated herein by reference.

NAMES OF THE PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are 1) Consejo Superior de Investigaciones Cientificas and 2) Universidad Complutense de Madrid.

BACKGROUND OF THE INVENTION

Field of the Invention

The invention relates to a hydrogel comprising vinyl caprolactam and at least two crosslinkers. These hydrogels, which may contain, or not, other additional monomers, favor cell growth and allow for the subsequent detachment of cells and layers of cells using thermal stimuli. These hydrogels exhibit great potential, specially the hydrogel without additional monomer, because it is robust, very manageable and flexible. This invention also relates to the application of these materials as supports for cell culture and transplantation.

Description of the Related Art

Tissue engineering and regenerative medicine require available and robust technologies for cellular manipulation. The in vitro harvesting of cells and cell layers requires robust methodologies capable of holding cells to confluence and further delivering the cells or layers of cells in a non aggressive manner, in contrast to traditional and potentially harmful methods using cell enzymes or scraping, which can damage the cells. One of these non aggressive methodologies is based on the use of heat sensitive substrates based on Poly N-isopropylacrylamide (pNlPAm), capable of holding cells to confluence and providing a detachment of cells and cell layers induced by a decrease in temperature. A cell layer detached in this manner maintains its cell to cell and cell to extracellular matrix (ECM) junctions, thereby mimicking the native architecture of tissues so that these cell layers can be used for two dimensional (2D) or three dimensional (3D) biomedical constructions or in tissue damage reparation.

However, in many techniques depending on pN1PAm based coatings, adhesion is produced depending on the cell thickness (preferably, ultra thin grafts), which cause these supports to be expensive and complex. Therefore, it remains necessary to develop more alternatives for soft detachment of cells and cells layers.

An alternative heat sensitive polymer is poly vinyl caprolactam (pVCL), which exhibits Lower Critical Solution Temperature (LCST) values similar to pNIPAm (in a physiologically relevant range also) and cytocompatibility. Lee et al. (Lee, B.; Jiao, A.; Yu, S.; You, J. B.; Kim, D.-H.; Im, S. G., *Initiated chemical vapor deposition of thermoresponsive poly (N-vinyl caprolactam) thin films for cell sheet engineering, Acta Biomaterialia;* 2013; 9(8): 7691-7698) disclosed the preparation of thin pVCL films (about 50 nm) on Nylon fabric substrates, obtaining only partial detachment of the cell layer. Lim et al (Lim, Y. M.; Jeun, J. P.; Lee, J. H.; Lee, Y. M.; Nho, Y. C., *Cell sheet detachment from poly (N-vinyl caprolactam-co-N-isopropylacrylamide) grafted onto tissue culture polystyrene Dishes*. Journal of Industrial and Engineering Chemistry 2007, 13 (1), 21-26) grafted copolymers of NIPAm and VCL into PS (polystyrene) plates and achieved cell layer detachment.

Yang et al (Polymer Chemistry, 2015; 6 (18): 3431-3442) prepared VCL hydrogels with a zwitterionic methacrylate, which were capable of detaching cells by lowering the temperature. However, this study was limited to the use of a zwitterionic methacrylate as additional monomer. Cell adhesion on its materials with zwitterions prevents cell spreading on the surface. After 7 days a dense monolayer is not achieved, but growth in more or fewer clusters and their cells doubling the metabolic activity. With the pVCL, with zwitterions, a nearly complete detachment at 2 h at 4° C. or 25° C. is achieved U.S. Pat. No. 4,436,887 discloses vinyl lactams polymers comprising at least one crosslinker which is a di cyclic compound (alkenyl tertiary amine) free of resonant forms, which can be represented by the formula $CH_2$:CG $(CH_2)_x$ N~J~N$(CH_2)_x$ CG:$CH_2$, wherein x is 0 or 1, G is hydrogen or methyl and the group J is a group with a cyclic structure forming a dialkene urea, dialkene hydrazide, dialkene amide, dialkene hydantoin, dialkene hydrouracil or dialkene 2,2'-bisimidazoline. Said crosslinker is present in a molar percentage of at least 50% of the total amount of crosslinkers, in the event that there is some other crosslinking agent.

The document Ind. Eng. Chem Res 2010, 49, 11741-11751 discloses N vinyl Caprolactam gels in which diethylene glycol methacrylate and allyl methacrylate are used as the crosslinker, but both are not used simultaneously, therefore they are different from those of the present invention.

The main objective of the materials disclosed in this document is the manufacture of contact lenses, although they can be used in other medical use devices. But is not disclosed to be used as supports for growing cells, nor is the use of heat sensitivity in case that the vinyl lactam is vinyl caprolactam.

The materials of the invention based on VCL are not coatings like the NIPAm based coatings mentioned above, they are independent hydrogels, and do not have a thickness requirement nor require superstrate for the transplantation. These new hydrogels are hydrated systems capable of being loaded with active compounds, which can then be released in a controlled manner, and are mechanically robust. This robustness is associated with the use, according to the present invention, of at least two crosslinkers of different nature.

In addition to the mixture of crosslinkers, the structure of the hydrogels of the invention can be simply functionalized by incorporating additional monomers. These hydrogels, which are robust and easy to handle and manipulate, are obtained in a radical photopolymerization, or thermal, or redox process.

The hydrogel without additional monomers offers a high heat sensitivity and very good performance in culture and cell detachment. For these cellular systems, the use of hydrogels allowed to transplant the cells without the need of a superstrate, and without the need for a low thickness, these being the usual limitations for the use of polyN-isopropylacrylamide (pNIPAm) supports, such as commercial grafts In the case of additional monomers of the methacrylate ion type, the nature and type of charge have shown a great influence on cell growth. Although all of the hydrogels of the invention including additional ionic monomer (regardless of the type of ionic component) have been shown to be capable of forming cellular monolayers, especially the hydrogels with additional zwitterionic and pseudo-zwitterionic monomers have shown excellent detachment efficiency by lowering the temperature, close to that offered by the above-mentioned hydrogels without additional monomers. Using the VCL-based hydrogel with zwitterionic methacrylate as an additional monomer, the cells show an adherent and extended morphology, which favors the growth of the culture and the development of the monolayer. Cells reach six times the initial value in 3 days. In addition, dense, integral, viable and metabolically active monolayers are detached within only 45 min at 25° C.

The entire family of hydrogels that are the subject matter of the invention is a candidate to compete with the expensive and complex thermosensitive cellular platforms based on these pNIPAm grafts. The ability of the surfaces of these hydrogels to allow cell harvesting is related to the early molecular interactions during the early binding process. Once the cell-surface interaction is established, complete detachment of the cell layer is only possible if the traction strength of the cytoskeleton predominates over the surface attraction. In this sense, each material exhibits numerous, often uncontrolled, interactions with proteins and cells in vitro and in vivo, leading to several conclusions and determinations regarding the “biocompatibility” of the materials.

DESCRIPTION OF THE INVENTION

The expression “based on” should be understood as “formed by” or “formed from”, that is to say that the constituents of the product referred to, may not be in the initial state in which they were used to obtain said product; in particular, this last clarification refers to the fact that after polymerization the monomeric precursors become part of the macromolecular skeleton as repetitive units. It can be considered an expression equivalent to “comprises”, taking into account that a monomer is forming part of a polymer in the form of a repetitive unit. This is what is meant by the expression “based on”.

The term “comprises” in Claim 1 means that the structures derived from VCLs and the crosslinkers are part of the polymer chains.

The expression “type” or “of type” should be understood as “similar to”, or comprising a particular functional group, for example “vinyl-lactam type” should be interpreted as including at least one lactam functional group, and includes any vinyl-lactam.

In this application the term “crosslinker”, refers to alkene or vinyl polymerizable derivatives with functionality equal to or greater than two, that is, containing at least two alkene groups polymerizable by radical route.

The term “additional monomer” should be understood as alkene derivative polymerizable by radical route with monofunctional character, i.e. with only one vinyl group, and different from vinyl caprolactam.

In this application the prefix (meth) is used before acrylic, acrylate or acrylamide, to encompass in the same term acrylic and methacrylic compounds, for example: (meth) acrylic acid encompasses both acrylic and methacrylic acid.

A first object of the present invention refers to a hydrogel characterized by comprising vinyl-caprolactam type monomers, and at least two crosslinkers, wherein a first crosslinker is selected from alkene(meth) acrylic (A) structures (a, R unsaturated structures) or divinylbenzene,

A

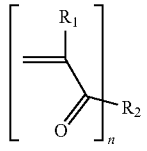

wherein:

$R_1$ is selected from hydrogen or methyl, $R_2$ is selected from di, tri, tetra or penta-substituted alkoxys, dialcoxy-disubstituted derivatives, a diaryloxy-substituted or non-substituted group, diaminoalkyl $C_1$-$C_6$ N, N' disubstituted or hexatriazine N, N', N" trisubstituted, n is selected from 2, 3, 4 or 5, and a second crosslinker is selected from the following vinyl-alkene structures, which comprise a vinyl-alkyl group or a vinyl group attached to a heteroatom (C, D)

C

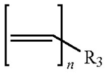

D

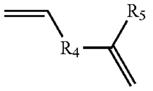

wherein:

$R_3$ is selected from dialkoxy $C_1$-$C_{12}$ disubstituted, dialkanoyloxy $C_1$-$C_{12}$ disubstituted, -imidazolin-2-one N, N'-disubstituted or 3,3'-(alkyl)-di-1-vinyl-2-lactam N, N'-disubstituted, n is selected from 2 or 3, $R_4$ is selected from an oxycarbonyl, carbonate or urea group, substituted or not with $C_1$-$C_4$ alkyl, alkoxy or alkanoyloxy groups, $R^5$ is selected from hydrogen or methyl such that in the case that $R_3$ is -imidazolin-2-one N, N' disubstituted, the second crosslinker is present in a molar ratio of less than 50% with respect to the crosslinker mixture, such that in the case that it comprises an additional crosslinker, such additional crosslinker is a crosslinker that has the formula of the first crosslinker or has the formula of the second crosslinker, and excepting the hydrogel formed by vinyl-caprolactam, potassium sulfopropyl methacrylate and the crosslinkers ethylene glycol dimethacrylate and 3,3'-(propyl)-di-1-vinyl-2-pyrrolidone.

According to the present invention, in the event that a crosslinker coincides with that described earlier in U.S. Pat.

No. 4,436,887, said crosslinker is present in a molar percentage of less than 50% with respect to the crosslinker mixture.

In a preferred embodiment, hydrogel is characterized because it also comprises at least one additional monomer.

The hydrogel of the invention comprises at least one crosslinker of each of these two types, and may comprise combinations thereof.

As an example, different substituents are described for the structures selected for $R_2$:

- di, tri, tetra or penta alkoxy substituted respectively 2, 3, 4 or 5 times with the structure $R_1C{=}CH_2$ according to formula A; linear or branched di, tri, tetra or penta alkoxy $C_1$-$C_{12}$, optionally substituted with one or more hydroxy, phosphate, urethane, polysiloxane, isocyanurate, oligo(ethoxy)$_m$, (oligopropoxy)$_m$, oligo(glycerol)$_m$ groups (wherein m is 1,2,3,4,5). As an example, alcoxi derivatives of ethylene glycol, butanediol, pentanediol, nonanediol, tricyclodecane dimethanol, decanediol, hexanediol, trimethylolpropane, pentaerythritol, glycerol, dipentaerythirol, neopentilglycol,
- dialcoxy derivatives disubstituted with the structure $R_1C{=}CH_2$ according to formula A, from oligo- or poly-ethylene oxide, oligo- or poly-propylene oxide, or block copolymers of both units. As an example, alkoxy derivatives of ethylene glycol, triethylene glycol, tetraethylene glycol, polyethylene glycol, polypropylene glycol, polyethylene glycol/polypropylene glycol block copolymer,
- a diaryloxy group (such as benzenediol oxy derivative, or bisphenol A) disubtituted with the structure $R_1C{=}CH_2$ according to formula A, not substituted or substituted with oligo(ethoxy)$_m$, (oligopropoxy)$_m$, oligo(glycerol)$_m$ groups (wherein m is 1,2,3,4,5)
- diaminoalkyl $C_1$-$C_6$ N, N' disubstituted with the structure $R_1C{=}CH_2$ according to formula A
- hexatriazine N, N', N" trisubstituted with the structure $R_1C{=}CH_2$ according to the formula A As an example, the various substitutes for the structures selected for $R_3$ are described:

- dialcoxy $C_1$-$C_{12}$ disubstituted with the structure $CH{=}CH_2$ of formula C; linear or branched, optionally substituted with one or more hydroxy, phosphate, urethane, polysiloxane, isocyanurate, oligo(ethoxy)m, (oligopropoxy)m, oligo(glycerol)m groups (wherein m is 1,2,3,4,5),
- dialkanoiloxy $C_1$-$C_{12}$ disubstituted with the structure $CH{=}CH_2$ of the formula C; linear or branched, optionally substituted with one or more hydroxy, phosphate, urethane, polysiloxane, isocyanurate, oligo(ethoxy)$_m$, (oligopropoxy)$_m$, oligo(glycerol)$_m$ groups (wherein m is 1,2,3,4,5),
- imidazolin-2-one N, N' disubstituted with the rest $CH{=}CH_2$ of the formula C,
- 3,3'-(alkyl)-di-1-vinyl-2-lactam N, N' disubstituted with the rest $CH{=}CH_2$ of the formula C; linear or branched alkyl $C_1$-$C_{12}$, optionally containing one or more ether or lactam groups; lactam can be pyrrolidone or caprolactam.

In a preferred embodiment, the first crosslinker is selected from ethylene glycol di(meth)acrylate, triethylene glycol di(meth)acrylate, tetraethylene glycol di(meth)acrylate, trimethylolpropane tri(meth)acrylate, bisphenol A di(meth) acrylate, ethoxylated bisphenol A di(meth)acrylate, pentaerythritol tri-, and tetra(meth)acrylate, tetramethylene di(meth)acrylate, N,N'-methylenebisacrylamide, divinyl benzene, polysiloxanylbisalkyl (meth)acrylate, diurethane dimethacrylate, polyethylene glycol di(meth)acrylate, and combinations thereof.

In a preferred embodiment, the second crosslinker is selected from vinyl carbonate, triallycyanurate, methacryloxyethyl vinyl urea, diallyl itaconate, diallyl phthalate, N,N-dialylacrylamide, vinylmethacrylate, alylmethacrylate, divinyl adipate, divinyl pyrrolidone derivatives, 1,3-divinylimidazolin-2-one and combinations thereof.

The mixture of at least two crosslinkers of different nature, provides robustness to the hydrogel.

In a preferred embodiment, each one of the crosslinkers is present in concentrations in the range 0.01-20% molar with respect to the total monomer moles.

Preferably, the crosslinkers are ethylene glycol dimethacrylate and 3,3'-(propyl)-di-1-vinyl-2-pyrrolidone.

In another preferred embodiment, crosslinkers are preferably ethylene glycol dimethacrylate and 1,3-divinylimidazolin-2-one.

In another preferred embodiment, at least one crosslinker is an acetal group carrier compound.

In a more preferred embodiment, the first crosslinker is (((4-hydroxyphenyl)methylene)bis(oxy))bis(ethane-2,1-diyl)bis(2-methacrylate) and the second 3,3'-((phenylmethylene)bis(oxy))bis(propane-3,1-diyl))bis(1-vinylpyrrolidin-2-one). The hydrogels containing these two crosslinkers are resorbable. This is associated with the hydrolytic character of the structures of both crosslinkers, which allows the hydrogel to break with the final result of soluble chain formation.

In another preferred embodiment, hydrogel comprises as additional monomers polymerizable alkene derivatives with a single polymerizable functionality.

In a preferred embodiment, the additional monomer is selected from maleimides, maleic acid, fumaric acid, maleates, fumarates or alkene (meth)acrylic structures.

In a preferred embodiment, the additional monomer is an alkene (meth)acrylic structure,

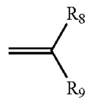

wherein $R_8$ is selected from hydrogen or methyl, $R_9$ is selected, for example, from a nitrile group, carboxylic acid, a substituted ester group, an amide group, a N substituted amide group, a N N' disubstituted amide group, a non-substituted or substituted aryl group, an oxycarbonyl substituted group, an oxy substituted group, a substituted amine, a substituted amino carbonyl group, a nitrogen bound N-lactam group, formamide, phosphonic, sodium sulfonate, acetamide, carbazole, imidazole, trimethylsilane or pyridine.

As an example, the different substitutes for the structures selected for $R_9$ are described:

- a nitrile group, carboxylic acid,
- an ester group substituted with an alkyl $C_1$-$C_{12}$ group, linear or branched, optionally substituted with one or more halogen, hydroxy, amino, amino hydrochloride, carboxy, carboxylate, alkyl, sulfonic, sulfonate, quaternary amine salt, phosphate, zwitterionic betaine type structure, phosphorylcholine structure, diethylamino, dimethylamino, alkoxy, aryl, aralkyl, amine, alkylamino, dialkylamino groups
or a silylated derivative (such as trimethylsilyl),
or succinimide,
oligoester or ethylene polyoxide, propylene oligo- or polyoxide or block copolymers of both units, hydroxy, methyl or ethyl as terminal group
an amide group,
an N-amide group substituted with a $C_1$-$C_{12}$ alkyl group, linear or branched, optionally substituted with one or more halogen, hydroxy, amino, amino hydrochloride, carboxy, carboxylate, alkyl, sulfonic, sulfate, quaternary amine, phosphate, zwitterionic betaine type structure, phosphorylcholine structure, diethylamino, dimethylamino, alkoxy, aryl, aralkyl, amine, alkylamino, dialkylamino groups,
an N, N amide group substituted with two $C_1$-$C_{12}$ alkyl groups (such as methyl or ethyl), linear or branched, optionally substituted with one or more halogen, hydroxy, amino, amino hydrochloride, carboxy, carboxylate, alkyl, sulfonic, sulfate, quaternary amine salt, phosphate, zwitterionic betaine type structure, phosphorylcholine structure, diethylamino, dimethylamino, alkoxy, aryl, aralkyl, amino, alkylamino, dialkylamino groups,
an aryl group (such as phenyl) not substituted or substituted with one or more alkyl $C_1$-$C_3$, halogen, alkoxy, carboxy, carboxylate, sulfonic, amino, sulfonate groups,
an oxycarbonyl group substituted with an aryl or alkyl $C_1$-$C_{12}$ group, linear or branched, optionally substituted with one or more halogen, hydroxy, amino, amino hydrochloride, carboxy, carboxylate, alkyl, alkoxy, aryl, aralkyl, alkylamino, dialkylamino groups,
an oxy group substituted with an aryl or alkyl group $C_1$-$C_{12}$, linear or branched, optionally substituted with one or more halogen, hydroxy, amino, amino hydrochloride, carboxy, carboxylate, alkyl, alkoxy, aryl, aralkyl, alkylamino, dialkylamino groups,
an amine substituted with an aryl or alkyl $C_1$-$C_{12}$ group, linear or branched, optionally substituted with one or more halogen, hydroxy, amino, amino hydrochloride, carboxy, carboxylic acid salts, alkyl, alkoxy, aryl, aralkyl, alkylamino, dialkylamino groups,
an amino carbonyl group substituted with an aryl or alkyl $C_1$-$C_{12}$ group, linear or branched, optionally substituted with one or more halogen, hydroxy, amino, amino hydrochloride, carboxy, carboxylate, alkyl, alkoxy, aryl, aralkyl, alkylamino, dialkylamino groups,
a N-lactam group, bound by nitrogen. The lactam can be a ring of 5, 6, 7, substituted or unsubstituted in position 3 with alkyl groups $C_1$-$C_{12}$, linear or branched, optionally substituted with one or more halogen, hydroxy, amino, amino hydrochloride, carboxy, carboxylate, alkyl, sulfonic, sulfonate salt, quaternary amine salt, phosphate, zwitterionic betaine type structure, phosphorylcholine structure, diethylamino, dimethylamino, alkoxy, aryl, aralkyl, amino, alkylamino, dialkylamino groups,
or carbonyl, sulfone, ester, amide groups,
formamide, phosphonic, sodium sulfonate, acetamide, carbazole, imidazole, trimethylsilane or pyridine.

In a more preferred embodiment, the additional monomer is selected from the following (meth)acrylic structures: hydroxyethyl(meth)acrylate, (meth)acrylic acid, potassium sulfopropylacrylate, ethylphosphate monoacrylate, oligoethylene glycol (meth)acrylates, trimethylsilyl methacrylate, polyethylene glycol (meth)acrylates, N,N dimethylacrylamide, acrylamide, alkyl (meth)acrylate (wherein alkyl is an alkyl group with n carbon atoms being n=1,2, . . . 12), N-isopropylacrylamide, hydroxypropylmetacrylamide, N-dodecylacrylamide, N-(3-aminopropyl)methacrylamide hydrochloride, 2-aminoethyl (meth)acrylate hydrochloride, 2-(N,N-diethylamino)ethyl (meth)acrylate, N-(meth)acryloylsuccinimide, sodium 2-acrylamide-2-methyl-1-propanesulfonate, 2-acrylamide-2-methyl-1-propanesulfonic, [2-((meth)acryloxy)alkyl]trimethylammonium salts, zwitterionic sulphobetaine methacrylate, zwitterionic sulphobetaine methacrylamide, phosphorylcholine methacrylate, methacryloyl-L-lysine, carboxyethylacrylate, 2-sulfoethylmetacrylate, and combinations thereof.

In a preferred embodiment, the additional monomer is a styrenic structure.

In a more preferred embodiment, the styrenic structure is selected from styrene, chlorostyrene, bromostyrene, vinylaniline, vinylnaphthalene, vinylbenzoate or vinylanisole.

In an additional preferred embodiment, the additional monomer is a vinyl structure containing a vinyl attached to heteroatom.

In a further preferred embodiment, the vinyl structure containing a heteroatome-bound vinyl is selected from N-vinylacetamide, vinylpyrrolidone, vinylcarbazol, vinylpyridine, vinylimidazole, vinyl acetate, vinylformamide, vinylphosphonic, sodium vinylsulfonate or vinyltrimethylsilane.

In a preferred embodiment, hydrogel comprises combinations of the different additional monomers.

In a preferred embodiment, the molar ratio vinyl-caprolactam/additional monomers is in the range 2/1 to 1000/1, preferably 2/1 to 100/1.

In a preferred embodiment, the crosslinkers are used in a percentage between 0.01% and 20% in moles of the total monomer content.

Another aspect of the invention concerns a process for obtaining the hydrogel defined in the first aspect of the invention.

The process comprises at least the following steps:
a) mixing the vinyl caprolactam monomers, one or more additional monomers, if present, solvent, if present, and at least two crosslinkers,
(b) bubbling the mixture (a) with a gas,
c) transfer of the product obtained in stage b) to a mold,
d) polymerization, and
(e) swelling of the product obtained in (d) by immersion in water or in alcohols or water/alcohol mixtures.

A radical polymerization can be differentiated in the initiation mode: it can be photoinitiated, or thermally initiated, or initiated by the use of a redox pair, or by other methods. On another level, the type of radical polymerization can also be distinguished in terms of components: solution polymerization if there is a solvent, or mass polymerization if there is no solvent.

In a preferred embodiment, the polymerization is carried out in a photocuring chamber and the UV radiation is maintained between 0.01 and 60 minutes.

In a preferred embodiment, polymerization is carried out without solvent addition (step a). That is, mass polymerization.

In a preferred embodiment, polymerization is carried out at a temperature between 30° C. and 120° C. for a time between 0.1 and 24 hours. That is, it is done by thermal initiation.

Another aspect of the invention concerns the use of hydrogel for obtaining cell cultures and transplants materials. In a preferred embodiment, the endothelial cell line or the osteoblastic cell line are used.

Unless otherwise stated, all technical and scientific terms used in this application have the same meaning commonly understood by one of the experts in the field to which this invention belongs. Similar or equivalent methods and materials to those described herein may be used in practice in the present invention. Throughout the description and claims, the word "comprise" and its variations are not intended to exclude other technical characteristics, additives, components or steps. Additional objects, advantages and characteristics of the invention will become evident to the experts in the field after the examination of the description or can be learned through the practice of the invention. The following examples and illustrations are provided for illustration purposes and are not intended to be limiting to the present invention.

EXAMPLES

Figure 1:
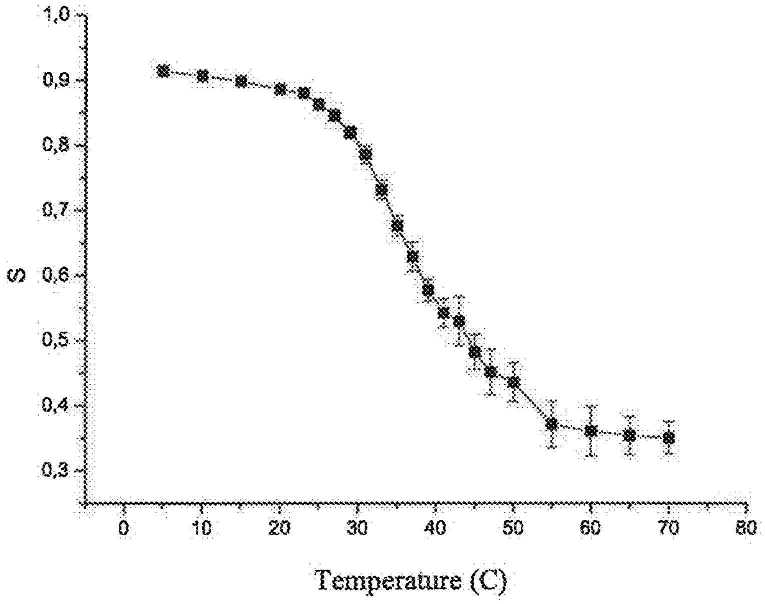
FIG. 1. Temperature-dependent S swelling for the VCL-based hydrogel without additional monomers, described in Example 1.

Next, the invention will be illustrated by means of some experiments carried out by the inventors, which show the effectiveness of the subject-matter of the invention.

Materials and Methods

The potassium sulfopropylmethacrylate (M-$SO_3$—), the solution of [2-(methacryloxyloxy)ethyl] trimethylammonium chloride (M-$N^+$), [2-(methacryloxyloxy)ethyl]dimethyl(3-sulfopropyl)ammonium hydroxide (M-$N^+$—$SO_3$—), 2-methacryloxyethyl phosphorylcholine (M-$PO_3$—$N^+$), hydroxyethyl methacrylate (M-OH), methacrylic acid (M-COOH), vinyl caprolactam (VCL), ethylene glycol dimethacrylate (C1), 1-hydroxy cyclohexyl phenyl ketone (HCPK) and azobisisobutyronitrile (AIBN) used in the examples were acquired from Sigma (Sigma-Aldrich, St. Louis, Mo.). The monoacryloyloxy ethyl phosphate (M-$PO_4H_2$) was supplied by Polysciences. The 1,3-divinylimidazolin-2-one (C2') was supplied by BASF. C166-GFP (green fluorescent protein) was obtained from ATTC (ATCC® CRL-283™), fetal bovine serum of Thermus (Hyclone®, Thermo Scientific, Waltham, Mass.) and DMEM and antibiotics (penicillin, streptomycin and G418) from Sigma. The 24-well plates (treated and untreated) and 6-well plates were purchased from Corning Costar (New York, N.Y.), all other plastic objects for cell culture were obtained from Deltalab (Spain).

3,3'-(propyl)-di-1-vinyl-2-pyrrolidone (C2) was synthesized following a protocol similar to that previously described in our laboratory for other VP derivatives: A solution of N, N-diisopropyl amine (7.0 ml, 50.0 mmol) was cooled in anhydrous THF (80 ml) under an inert atmosphere at −78° C., then n-BuLi (17.3 ml, 43 mmol) was slowly added. After shaking for 10 minutes at 0° C., it was cooled again to −78° C. and a freshly distilled solution of VP (5.0 ml, 43 mmol) was added dropwise and shaken for 1 h. After the formation of VP enolate, 1,3-dibromopropane (1.1 ml, 10.75 mmol) in THF (20 ml) was added dropwise. This solution was then allowed to reach room temperature and was shaken for 24 h. Then the solution was hydrolyzed in en $CH_2Cl_2/H_2O$ (1:1.80 ml). The aqueous layer was extracted with $CH_2Cl_2$ (2×100 ml), the organic layers were combined and dried on $Na_2SO_4$ and the solvent was evaporated at reduced pressure. The residue was purified by column chromatography (silica gel, $CH_2Cl_2$ to $CH_2Cl_2$: $Et_2O$ 20:1) to give C2 (1,184 g, 42%) as a yellowish unctuous solid.

$^1H$ NMR (400 MHz, $CDCl_3$) δ 7,08 (dd, J=16,0, 9.1 Hz, 2H, CH═$CH_2$), 4,43 (d, J=9.1 Hz, 2H, CH═CHHcis), 4,39 (d, J=16.0 Hz, 2H, CH═CHH trans), 3,50 (td, J=9,8, 3.1 Hz, 2H, N—CHH), 3,38 (dt, J=9,8, 8.0 Hz, 2H, N—CHH), 2,58-2,46 (m, 2H, CO—CH), 2,36-2,24 (m, 2H, N—$CH_2$CHH), 1,82-1,97 (m, 2H, VP—CHH), 1,81-1,67 (m, 1H, m, 2H, N—$CH_2$CHH), 1,58-1,37 (m, 4H, VP—CHH y VP—$CH_2$—$CH_2$—$CH_2$—VP).

$^{13}C$ NMR (101 MHz, $CDCl_3$) δ 175,1 (C═O), 129,7 (CH═$CH_2$), 94,3 (CH═$CH_2$), 43,0 (N—$CH_2$), 42,3 (CO—CH), 31,1 (VP—$CH_2$), 24,8 (VP—$CH_2$—$CH_2$—$CH_2$—VP), 24,6 (CO—CH—$CH_2$).

HRMS (ESI) calculated for $C_{15}H_{22}N_2O_2$ 262,1681 found 263,1757 $[M^+H]^+$ y 285,1576 $[M^+Na]^+$.

VCL-based hydrogels were synthesized in one step by conventional mass radical photopolymerization or using Milli-Q water or water/ethanol mixtures as solvents. In the case of solvent use, a solution of VCL (6 mol/l) and, if applicable, M (any of the methacrylates or mixture thereof, 1, 0.5, 0.25 or 0.05 mol/l) was prepared, and the crosslinkers C1 and C2 (or C1 and C2') were added in appropriate proportions and in the range 1-4% mol (vs. total monomer content). 1-hydroxy-cyclohexylphenylketone (HCPK) was used as a photoinitiator (0.5% w/w of total monomers). The reaction mixtures were bubbled with $N_2$ and transferred by syringe to the appropriate molds. In the case of films, the polypropylene molds were separated with silicone spacers with a thickness between 0.3 and 1 mm. The photopolymerization was carried out for 40 minutes under UV radiation (λ=365 nm) in an ultraviolet UVP lamp (model CL-1000L, 230V). After photopolymerization, the nets were recovered from the molds and allowed to expand in Milli-Q water until equilibrium was reached. They were then thoroughly washed with water to remove any soluble material. For cell response studies, the samples were kept in ethanol at 4° C. until needed for experimentation. 24 h before the different experiments, the samples were again transferred to Milli-Q water and washed several times until the ethanol was completely removed.

Swelling Experiments

Swelling experiments were carried out on hydrogels based on VCLs prepared as explained above, in distilled water depending on temperature (5-70° C.) by means of gravimetry. The samples were allowed to swell for one day at each temperature to allow for equilibrium swelling at that particular temperature. The measurements were carried out in triplicate. The degree of swelling was determined according to the following expression:

$$(S,\%) = \frac{W_t - W_0}{W_t} \qquad \text{(eq. 1)}$$

wherein Wt and W0 are the weights of the swollen (at each temperature) and dry samples, respectively. The volume phase transition temperature, VPTT, was defined as the beginning of the curve, that is, the temperature of the intersection of the initial situation and the line of adjustment of the points from the region near the turning point, where the initial situation is below the transition temperature. VPTT is the valid parameter to describe the LCST type thermosensitivity in the nets.

Mechanical Properties of Hydrogels

The mechanical properties of the VCL-based hydrogels prepared as explained above, were measured by dynamic compression. This technique involves placing the material between two plates and compressing it. In a compression test, there is a linear region in lower deformations, wherein the material follows Hooke's law. In this region, Young's modulus can be calculated.

Compression measurements were carried out on gels swollen with water at equilibrium at 25° C. on an MTS® QTest1/L Elite test machine equipped with a 100 N load cell in compression mode. All hydrogel samples were prepared in a cylindrical form in its equilibrium swelling state with a diameter of 6 mm (and a sample thickness of 1 mm). For compressive testing of the hydrogels, the samples were completely immersed in a water bath and placed between compression plates where the upper sample has a diameter of 5 mm. Each sample was subsequently deformed at 0.1 mm/min. To obtain statistically reliable results, all measurements were made on 5 samples from each hydrogel system.

Preparation of Hydrogels for Cell Culture

All VCL hydrogels were sterilized with a 70% ethanol solution by rinsing six times for 10 minutes each time. They were then washed six times with PBS, exposed to UV radiation for 30 minutes on each side of the hydrogel, and washed twice with Dulbecco-modified Eagle's medium (DMEM) with high glucose content (D6429). In order to simulate the temperature of the culture conditions (37° C.), above the LCST, a hot plate with a constant temperature was used for the material cutting process, obtaining 2 $cm^2$ samples that fit the 24-well plates (Corning Costar).

After cutting, the samples were left in an overnight incubation at 37° C. and 5% $CO_2$ with DMEM 10% fetal bovine serum (FBS) and 1% antibiotic (100 U/ml penicillin and 100 μg/ml streptomycin sulfate).

Cell Culture

C166-GFP (ATCC® CRL-2583™) is a mouse endothelial cell line transfected with green fluorescent protein (GFP). The culture conditions are DMEM enriched with 10% fetal bovine serum plus 1% antibiotic (penicillin and streptomycin sulfate) and 0.2 mg/ml of G-418 antibiotic to the culture medium for the selection of GFP retaining cells. The cells were seeded in the nets with a density of $1.5\times10^4$ cells/$cm^2$ and incubated at 37° C. with 5% $CO_2$. The cells were monitored using an inverted fluorescence microscope (Olympus IX51) with a FITC filter (λex/λem488/568 nm).

Methodology for Cell Sheet Thermal Detachment

All cell culture hydrogels evaluated with cells in examples 4 to 7, which were prepared as described in examples 1,2 and 3, as well as in examples 6 and 7, were placed upside down and placed in new TCP (tissue culture plates) wells. After this, cold medium was added to each well in order to reach T527° C. A temperature probe (SC1, Biocote, UK) was used to monitor this process. After 45 min, the hydrogels were extracted and the samples were re-incubated at 37° C. with $CO_2$.

Characterization of Transplants

The transplanted cells were daily observed using an inverted fluorescence microscope (Olympus IX51) and microphotographs were taken.

Alamar Blue

The metabolic activity of cell transplants was measured with an Alamar Blue assay, following the manufacturer's instructions (Biosource, Calif., USA). This method is non-toxic, scalable, and uses the natural reducing powder of living cells, generating a quantitative measure of cell viability and cytotoxicity. In summary, Alamar Blue dye (10% of culture volume) was added to each well, containing live transplanted cells, and incubated for 90 minutes. Tests were carried out on each type of sample in triplicate. The fluorescence (λex/λem 535/590 nm) of each well was measured using a plate reader (Synergy HT, Brotek).

The hydrogels listed in Table 1 were evaluated as supports for cell culture using mouse C166-GFP endothelial cells. C166-GFP cells were selected for this study as an adherent model line. This model generates a monolayer of cells with strong adhesion to the substrate. The cells were allowed to develop for 72 h at 37° C. above the VPTT of the hydrogels. Once the cell monolayer was formed, the hydrogels were observed using fluorescence microscopy and placed upside down in another tissue culture plate (TCP). In order to study the detachment of the cells, the hydrogels were cooled slightly to 20° C., below the VPTT using cold culture medium, at a temperature of 25° C. or below. The temperature was monitored using a temperature probe. Finally, the cell monolayer was detached as a result of the expansion of the hydrogel and transplanted onto a TCP (tissue culture plate) surface. At 48 hours after transplantation, the culture was observed using optical microscopy and metabolic activity was measured using an Alamar blue test.

Figure 3:
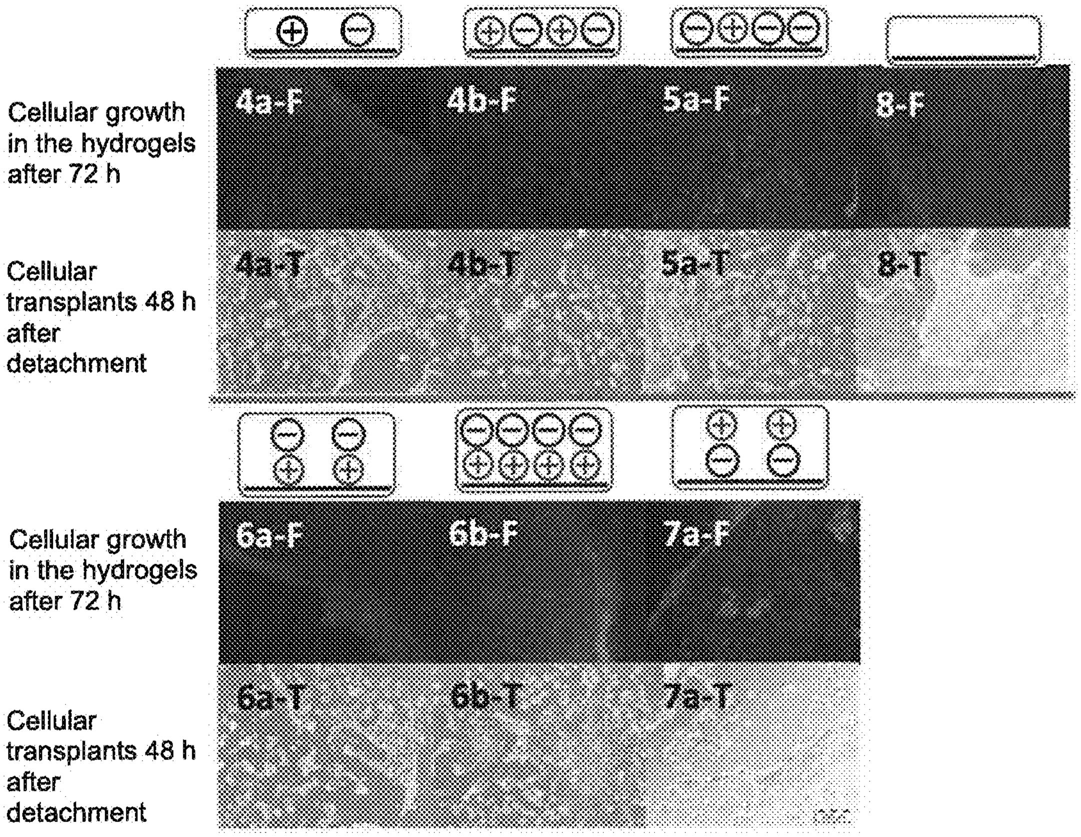
FIG. 3. Label 'F' refers to images obtained by culture fluorescence microscopy on samples 4, 5, 6, 7 and 8 of Table 1. Label 'T' refers to images obtained by optical microscopy of cells 48 hours after transplantation. Scale=200 μm.

Fluorescent and optical microscopies were used to evaluate the processes of cell development and transplantation. The images of the cell cultures in the different hydrogels taken after 72 hours, in addition to the optical images obtained for the transplants after 48 hours can be seen in FIG. 3. It is worth mentioning that the cell culture time, set at 72 h for all the experiments, was chosen in order to facilitate an early proliferation analysis of the cells. Likewise, the surface of the hydrogel was observed after the detachment process in order to determine the presence of residual cell monolayers and, consequently, to analyze the efficiency of the transplant. Finally, metabolic activity (Alamar blue) of cell transplants was observed 48 hours after the detachment process.

Example 1. Preparation of VCLs Based Hydrogels without Additional Monomers

A first series of LVC-based hydrogels was prepared according to the above described procedure under "Methods" and using ethanol or water/ethanol mixtures as the solvent, but without using additional monomer. A second series of VCL-based hydrogels was prepared according to the same procedure, but without the addition of solvent (mass polymerization).

In this case, to characterize the possible vitrification effect on the total conversion in this series by gravimetry, drying studies were carried out, and the final dry weight was compared with the precursor formulation mass. It was found that the conversion for this series was in the range 80-95%, while the first series that used solvent exceeded 95%. These hydrogels showed a high thermosensitivity in physiological temperature ranges (FIG. 1).

Example 2. Preparation of Hydrogels Based on LCVs with Different Ionic Methacrylates as Additional Monomers VCLs based hydrogels containing different ionic methacrylates (M) as additional monomers were prepared according to the procedure above described in Materials and Methods, with the molar ratios VCL/M indicated in Table 1, molar percentages of C1 and C2 of 2 and 0.1% respectively, with respect to the total monomers and using water/ethanol mixture as solvent. The structures of the precursors can be found in Table 1. Particularly relevant is the small percentage of 0.1% mole of the divinyl compound required to obtain robust hydrogels and prevent them from breaking during handling. As previously mentioned, C2 can play a key role in net properties because of its possible involvement in bonds between methacrylate-rich chains and VCL-rich chains.

TABLE 1

| | 2a | 2b | 3a | 3b | 4a | 4b | 5a | 5b | 6a | 6b | 7a | 7b | 8a |
|---|---|---|---|---|---|---|---|---|---|---|---|---|---|
| | ⊖⊖ | ⊖⊖⊖⊖ | ⊕⊕ | ⊕⊕⊕⊕ | ⊕⊖ | ⊖⊖⊖⊖ | ⊖⊕⊖⊖ | ⊕⊖⊕⊕ | ⊖⊖ ⊕⊕ | ⊖⊖⊖⊖ ⊕⊕⊕⊕ | ⊕⊕ ⊖⊖ | ⊕⊕⊕⊕ ⊖⊖⊖⊖ | — |
| Vinil - lactam | | | | | | VCL 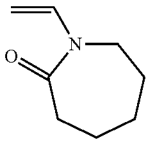 | | | | | | | |
| M | $M-SO_3^-$ 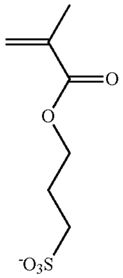 | | $M-N^+$ 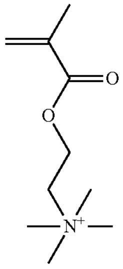 | | | | $M-SO_3^-1$ 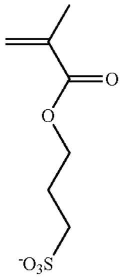 | | $M-N^+-SO_3^-$ 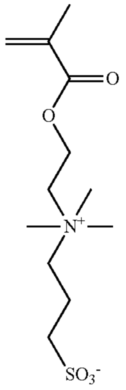 | | $M-PO_3^--N^+$ 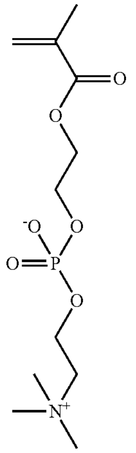 | | Sin M |
| VCL/M molar ratio | 12/1 | 6/1 | 12/1 | 6/1 | 12/1 | 6/1 | 6/1 | 6/1 | 12/1 | 6/1 | 12/1 | 6/1 | 12/1 |
| VPTT | 39 | 40 | 37 | 39 | 35 | 35 | 33 | 35 | 36 | 33 | 35 | 34 | 37 |
| Swelling 37° C. | 90 ± 3 | 89 ± 1 | 83 ± 2 | 91 ± 2 | 71 ± 1 | 69 ± 1 | 87 ± 1 | 87 ± 2 | 68 ± 2 | 61 ± 1 | 75 ± 1 | 82 ± 1 | 63 ± 2 |
| Crosslinkers structure | C1 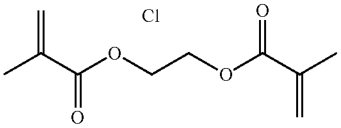 | | | | | | | | C2 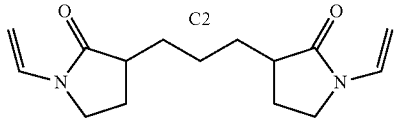 | | | | |

The molar ration $M-SO_3^-/M-N^+$ in systems 4a, 4b, 5a y 5b are 1/1, 1/1, 3/1 and 1/3 respectively.

Figure 2:
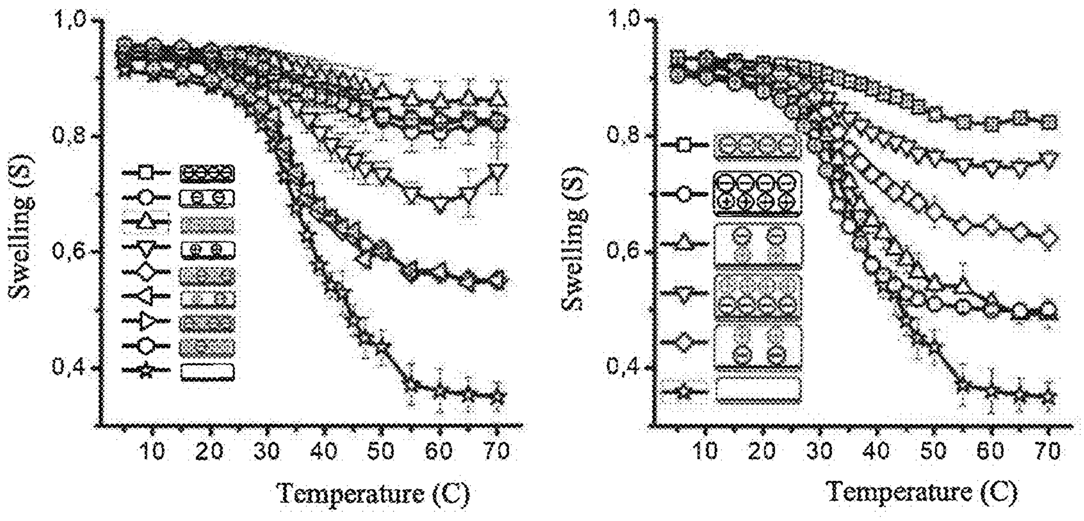
FIG. 2. Temperature-dependent S swelling for the hydrogels described in example 2 based on VCLs, with additional ionic methacrylate-type monomers.

Regardless of chemical compositions, all hydrogels exhibit thermosensitivity as shown in FIG. 2. This figure shows the temperature dependency of the samples. It is shown that the amount and type of additional monomer (M) has a strong influence on the degree of thermosensitivity (change in swelling capacity) but not on the volume phase transition temperature (VPTT) values. All samples have similar VPTTs, close to 37° C., this is, in a physiologically relevant range.

In terms of swelling, all samples exhibit similar swelling below the VPTT, i.e. in the 'hydrophilic' state, where the net is probably at its maximum expansion (the maximum value determined by the crosslink density). Above the VPTT, however, the type and amount of M has a strong influence on the swelling behavior and on the volume contraction, as mentioned above. On average, the incorporation of additional ionic monomers reduces the degree of thermosensitivity in a composition-dependent mode (the influence on swelling is greater for hydrogels with a 6/1 VCL/M molar ratio when compared to hydrogels with a 12/1 ratio), as it increases the hydrophilicity of the system. However, strong differences between the systems have been discovered. Hydrogels containing individual charges (negative samples 2 of Table 1, or positive samples 3) or excess of one type of charge (samples 5) exhibit less volume change than systems incorporating stoichiometric amounts of charges, i.e., zwitterionic sulfobetaine (samples 6), zwitterionic phosphorylcholine (samples 7), or pseudo-zwitterionic systems (samples 4). This difference must be related to the neutralization of charges in the latter group, while single-charged materials (or hydrogels with an excess of one type of charge) cannot avoid electrostatic repulsion among the units (maintaining a high degree of expansion) which, in addition to the intrinsic hydrophilicity of the ionic residues—reduces the contraction over the VPTT, in the 'hydrophobic' state. Zwitterionic phosphorylcholine does not correspond to the case of full charge neutralization, since the phosphate group has a low pK and does not completely ionize, in accordance with its change in intermediate volume. All these differences above the VPTT between the different hydrogels take place, to a lesser degree, at culture temperature, 37° C., which is an intermediate temperature. The swelling values at this temperature have been compiled in Table 1 to support the analysis below.

It has been observed that the water content, and consequently the hydrophilic/hydrophobic equilibrium, at 37° C. varies significantly for the different systems, which can also be very relevant for the cellular response. In particular, it can be observed that those hydrogels that carry additional charged monomers and have either a negative or positive net charge exhibit higher S-swelling values, (see Eq. 1), ranging from 89 to 91% (samples 2b and 3b). After charge neutralization, swelling is reduced from approximately 89-91% in series 2b, 3b to 69-71% in series 4.

The use of additional zwitterionic monomers requires a particular analysis. Hydrogels prepared using M—N+-$SO_3$— (6a and 6b) exhibit, as intended, low swelling compared to loaded hydrogels. Opposite to this observation, hydrogels prepared using M-$PO_3$—$N^+$ exhibited greater swelling.

Example 3. Preparation of VCLs Based Hydrogels Containing Combinations of Hydroxyethyl Methacrylate, Methacrylic Acid and Monoacryloxyethyl Phosphate as Additional Monomers The hydrogels were prepared according to the procedure indicated in Methods and Example 2. The prepared hydrogels are shown in Tables 2, 3 and 4. First, two series were obtained that contain MCOOH or M-OH as additional monomers, and a third series was obtained that contains both. For the first two series and to study the influence of the amount of additional monomer, 12/2, 12/1, and 12/0.5 VCL/M molar ratios were prepared. A control VCL based hydrogel was also prepared without additional monomers. It has been found that M-OH containing hydrogels are required to be demolded and washed in distilled water first. If ethanol was used for stripping and washing, the M-OH films probably broke down because of swelling stresses (which is higher in ethanol than in water). All hydrogels prepared in these three series are robust, transparent and easy to handle and maneuver.

TABLE 2

| | VCL/M-COOH 12:2 | VCL/M-COOH 12:1 | VCL/M-COOH 12:0.5 | VCL/M-COOH 12:0.25 | VCL/M-COOH 12:0.05 | VCL/M-OH 12:2 | VCL/M-OH 12:1 | VCL/M-OH 12:0.5 | VCL |
|---|---|---|---|---|---|---|---|---|---|
| | | | COOH COOH | | | | OH OH | | — |
| Vinyl-lactam main component | | | | | C | | | | |
| M | | | M-COOH<br>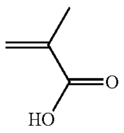 | | | | M-OH<br>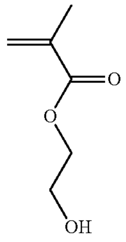 | | Sin M |

TABLE 2-continued

| | VCL/M-COOH 12:2 | VCL/M-COOH 12:1 | VCL/M-COOH 12:0.5 | VCL/M-COOH 12:0.25 | VCL/M-COOH 12:0.05 | VCL/M-OH 12:2 | VCL/M-OH 12:1 | VCL/M-OH 12:0.5 | VCL |
|---|---|---|---|---|---|---|---|---|---|
| VCL/M molar ratio | 12/2 | 12/1 | 12/0.5 | 12/0.25 | 12/0.05 | 12/2 | 12/1 | 120.5 | |
| Swelling 37° C. | 150% | 93% | 197% | 234% | 186% | 788% | 92% | 105% | 158% |
| VPTT (° C.) | 40.5 | 35.7 | 39 | 38.7 | 38.5 | 37.6 | 34.9 | 37.5 | 36.5 |
| Crosslinkers structures | 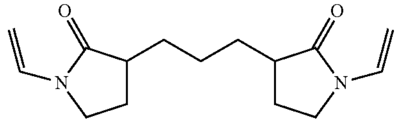 [SMILES: C=CN1CCC(CCCC2CCN(C=C)C2=O)C1=O] | | | | | 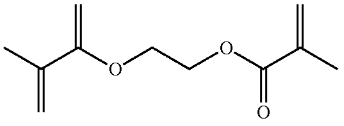 | | | |

TABLE 3

| | VCL/M-COOH 12:1:2 | VCL/M-COOH/M-OH 12:1:1 | VCL/M-COOH/M-OH 12:0.5:1 | VCL/M-COOH/M-OH 12:0.25:0.25 | VCL |
|---|---|---|---|---|---|
| | | | COOH OH | | — |
| Vinyl lactam Main Component | | | 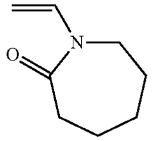 | | |
| M | | | M-COOH y M-OH 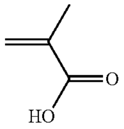 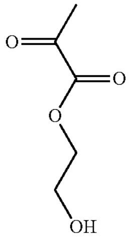 | | No M |
| Molar ratio VCL/M-COOH/M-OH | 12/1/2 | 12/1/1 | 12/0.5/1 | 12/0.25/0.25 | |
| Swelling at 37° C. | 35% | 97% | 94% | 149% | 158% |
| VPTT (° C.) | 35 | 37.9 | 36.9 | 34.9 | 36.5 |
| Crosslinkers structures | 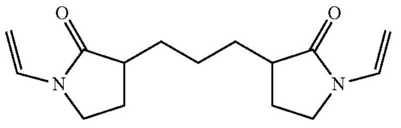 [SMILES: C=CN1CCC(CCCC2CCN(C=C)C2=O)C1=O] | | | 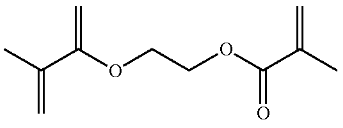 | |

Subsequently, hydrogels containing $M-PO_4H_2$ as an additional monomer were prepared. For this series, ethanol was replaced with triethylamine (TEA) to prevent vinyl groups degradation. TEA is an organic base capable of capturing the first proton of phosphoric acid, forming a salt. For this series, a complete optimization was carried out by replacing not only solvents but also the percentage of crosslinkers. Water was replaced by methanol (MetOH) increasing the hydrophobicity of the solution.

The hydrogels in this series are shown in Table 4. The specific changes made compared to the original formulation are detailed in each case. The amount and type of additional monomer (M) appear to have a great influence on the thermosensitivity, but not so much on the volume transition temperature (VPTT) values. All samples, including the hydrogel without additional monomer, have a similar VPTT, close to 37° C., which is a physiologically relevant range. The VPTT obtained in this study are similar to those reported in the literature for pure VCL systems.

TABLE 4

| | VCL/M-PO4H2 12:2 1.5% C1 | VCL/M-PO4H2 12:14% C1 | VCL/M-PO4H2 | VCL/M-PO4H2 12:1 0.4%/C2 | VCL/M-PO4H2 12:0.5 1.5% C1/ | VCL/M-COOH/M-PO4H2 | VCL/M-OH/M-PO4H2 | VCL/M-COOH/M-OH/M-PO4H2 | VCL/M-COOH/M-OH/M-PO4H2 | VCL |
|---|---|---|---|---|---|---|---|---|---|---|
| | | | $PO_4H_2$ $PO_4H_4$ | | | $PO_4H_2$ COOH | $PO_4H_2$ OH | $PO_4H_2$ COOH OH | | — |
| Vinyl-lactam | | | | | | VCL, 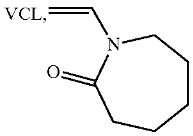 | | | | |
| M | | | M-$PO_4H_2$ 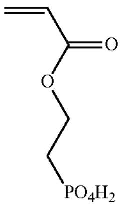 | | | M-COOH and M-$PO_4H_2$ 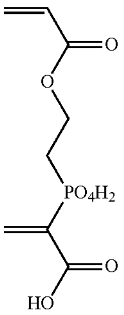 | M-OH and M-$PO_4H_2$ 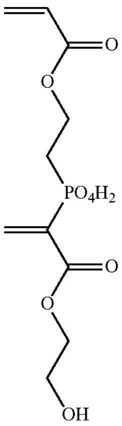 | M-COOH and M-OH and M-$PO_4H_2$ 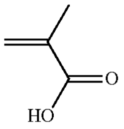 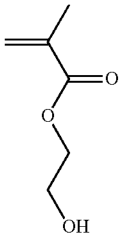 | 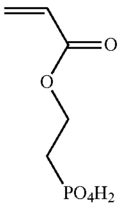 | Sin M |
| VCL/M-PO4H2/M-COOH/M-OH molar ratio | 12/2/0/0 | | 12/1/0/0 | | 12/0.5/0/0 | 12/1/1/0 | 12/0/1/1 | 12/1/1/1 | | |
| Swelling 37° C. ° C. (100*$w_{H2O}/w_{polygon}$) and VPTT (° C.) | | | | | 97% (40° C.) | 26.3% (39.5° C.) | 282% (35° C.) | 258% (41° C.) | 73% (35° C.) | 158% (36.5° C.) |
| Formulation changes, compared to series 1-3 | 1.5% C1 TEA:MetOH 1:1 | 4% C1 TEA:MetOH 1:1 | | 0.4%C2 TEA:MetOH 1:1 | 1.5%C1/ 0.4%C2 1:1 | TEA:MetOH 1:1 | TEA:MetOH 1/3:2/3 | 0.4%C2 TEA:MetOH 1.1 | 6%C1 TEA:MetOH 1.1 | |

Example 4. Cell Adhesion, Proliferation and Detachment Using VCL Hydrogels with and without Additional Ionic Methacrylate Type Monomers The total hydrogel load plays an important role in both modulating cell adhesion and proliferation, and also in cell detachment, which is also a crucial step in using the materials for cell manipulation and tissue modification. Moreover, different ionic charges can modulate cell adhesion through surface processes involving both adsorption of serum proteins and early cell adhesion. On the other hand, depending on the results demonstrated in the previous section, the type and amount of charge strongly influence the extent of thermosensitivity, mainly in terms of water absorption and volume change. Therefore, the hydrogel load can be very relevant in the potential cell detachment after the decrease of the temperature, which will be the property used for the detachment.

All VCL-based hydrogels without additional monomers allowed the adhesion and cellular proliferation of the following cell lines: C166-GFP endothelial cells, C2C12-GFP premioblastic cells and RAW264.7 macrophage cells. For most samples, a monolayer of cells is formed from the early stages (72 h), in case of adherent cell models. In the case of RAW 264.7 macrophages, optimal isolated cell growth has been observed, as expected with this non-adherent model. In the same way, viable cultures transplantations from the three lines were obtained by means of temperature decrease, both in monolayer and in isolated manner. In the analysis of VCL hydrogels with additional monomers, differences were observed in the adhesion and cell proliferation, as well as in the detachment in the hydrogel supports, depending on their composition.

When additional monomers with positive and negative charges are simultaneously included, either by stoichiometric combination of both units (pseudo-zwitterionic formulation, Table 1, samples 4) or by the use of zwitterion sulfobetaine (samples 6), a good cell proliferation of the C166-GFP endothelial model (images 4a and 4b of FIG. 3) is obtained, comparable or higher to the cell proliferation of hydrogel without additional monomer 8. There appears to be a compositional influence for samples 6 since the lower charged samples (6a) demonstrated a decreased surface charge effect on cell adhesion and proliferation compared to sample 6b. The detachment behavior (images 4a-T, 4b-T, 6a-T, 6b-T and FIG. 4) which is excellent for some of these samples (e.g. 6b) is consistent with the previous analysis. The cell transplants had, on average, the same or better quality than those obtained with sample 8 without additional monomer, with preserved ECM and cell junctions. The metabolic activities of transplants performed with sample 6b were clearly superior to those with sample 6a. In sample 6b, very few groups of small cells were detected in the hydrogel after detachment, suggesting an optimal detachment process (FIG. 5, image 6b-D). A similar situation is observed for hydrogels 6a, 4a and 4b after the detachment process, with smaller cellular aggregates adhering to the surface (FIG. 5, images 6a-D, 4a-D and 4b-D). In terms of thermosensitivity, these zwitterionic or (pseudo)zwitterionic samples 4 and 6 demonstrate a high volume change (although lower than the one exhibited by sample 8 without additional monomer), which is beneficial for monolayer detachment. Also, zwitterionic and pseudo-zwitterionic components are known to demonstrate anti-adhesive behavior. This anti-adhesive nature can also favor the detachment in the 'hydrophilic' state under the VPTT.

Figure 6:
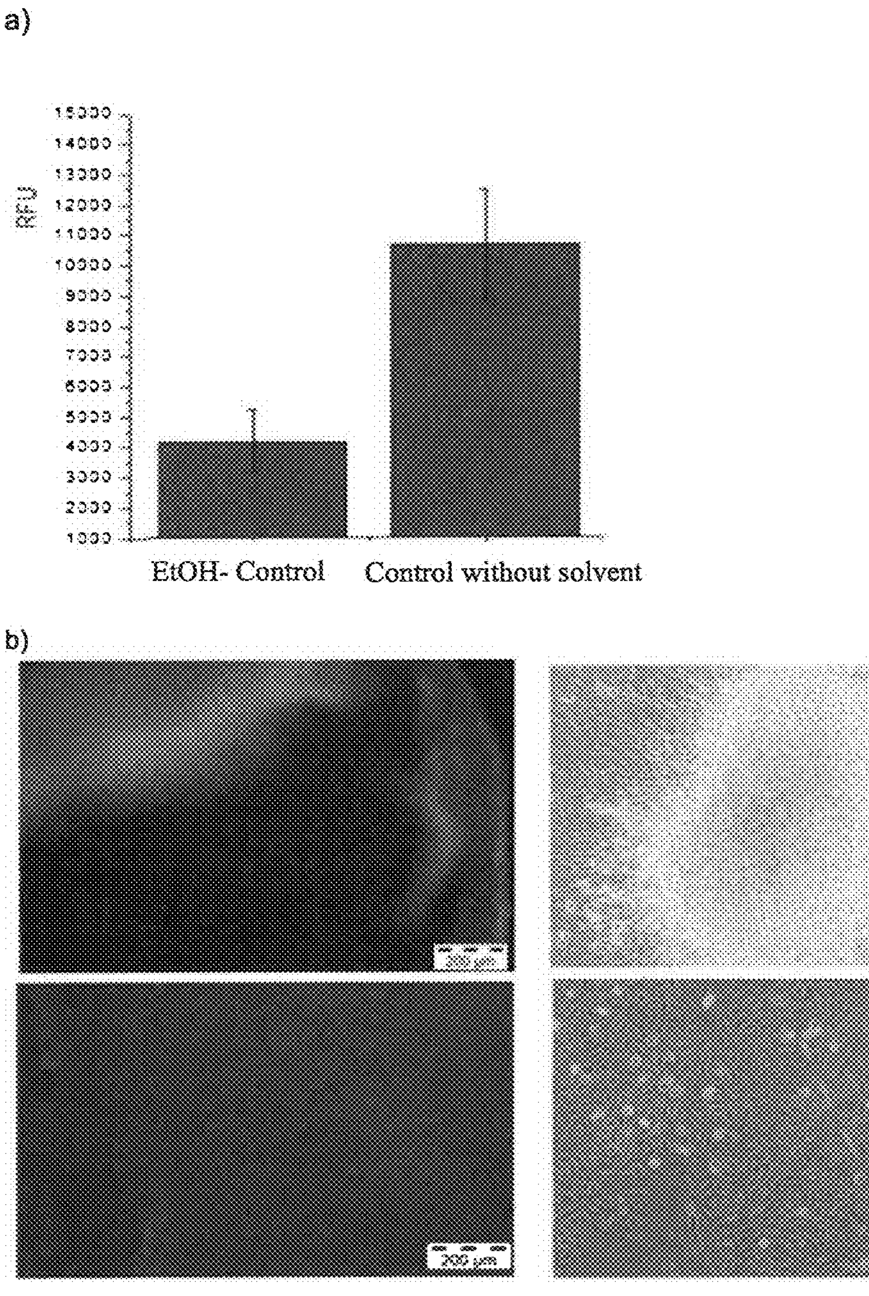
FIG. 6. A) Metabolic activity of transplants from solvent and mass-prepared VCL hydrogels. B) Images of the transplant and detachment, respectively for solvent and mass produced VCL hydrogels.

The cellular responses to hydrogels 5 (non-stoichiometric combination of positive and negative charges) and 7 (zwitterion phosphorylcholine) are consistent with the previous analysis. Sample 5a stands out, it presented a good transplantation capacity, with high metabolic activity readings (FIG. 6).

Example 5. Cell Adhesion, Proliferation and Detachment Using VCL Hydrogels with Different Molar Combinations of Hydroxyethymetacrylate, Methacrylic Acid and Monoacryloyl-Ethyl Phosphate To analyze biocompatibility, the hydrogels were tested with the C166-GFP endothelial line and with the MC3T3 osteoblastic line. First, the results obtained with the endothelial line will be detailed. All VCL/M-COOH surfaces allowed cell adhesion and proliferation of endothelial cells with some differences among the formulations. The VCL without additional monomer has demonstrated a well-developed monolayer with close cell junctions in accordance with the results shown in the example above. With the exception of the 12: 2 VCL/M-COOH this series of VCL/M-COOH hydrogels allowed the development of cell monolayers with high cell density and healthy appearance. In relation to transplantation, control with VCL hydrogel without additional monomer and 12: 0.25 VCL/M-COOH achieved optimal monolayer type transplantation.

The next family of hydrogels evaluated was VCL/M-OH. Again, all hydrogels allowed cell adhesion and proliferation of endothelial cells. With 12: 1 VCL/M-OH and 12: 0.5 VCL/M-OH formulations, large monolayers were found on the whole surface. VCL/M-OH 12: 1 resulted in good transplantation and double readings of metabolic activity after transplantation than those of VCL control without additional monomer.

The last series evaluated with an additional monomer was the VCL/M-$PO_4H_2$ series. In the VCL/M-$PO_4H_2$ hydrogels, the images revealed a good coverage of endothelial cells on the whole surface of the hydrogel, with cell cultures proliferating on the samples. In detail, large dense cell groups were found in 12: 2 VCL/M-$PO_4H_2$, 1.5% C1. The remaining hydrogels allowed the development of a monolayer, with a fast coverage on the surface of the material, except for 12: 1 VCL/M-$PO_4H_2$, 4% CL.

Transplantation behavior was analyzed, and 48 hours after detachment, larger cell monolayers were observed in 12: 2 VCL/M-$PO_4H_2$ 1.5% C1, 12: 1 0.4% C2 or 12: 0.5, 0.4% C2. 12: 1 4% C1, 12: 1 2% C1, and 12: 1 0.1% C2 2% C1. In terms of the metabolic activity of the transplanted surfaces, 12: 2 and 12: 0.5 are the highest measurements, they almost double the VCL transplants without additional monomer.

M-COOH, M-OH and/or M-$PO_4H_2$ combinations were evaluated. Proliferation on samples that included combinations of the different additional monomers, M-COOH, M-OH and/or M-$PO_4H_2$, was also developed into monolayers for VCL/M-COOH/M-OH 12: 0.5, VCL/M-OH/M M-$PO_4H_2$ and VCL/M-COOH/M-$PO_4H_2$. The samples VCL/M-COOH/M-OH 12: 0.5: 1; 12: 1: 2 and 12: 0.25: 0.25 resulted in large transplanted areas.

Figure 4:
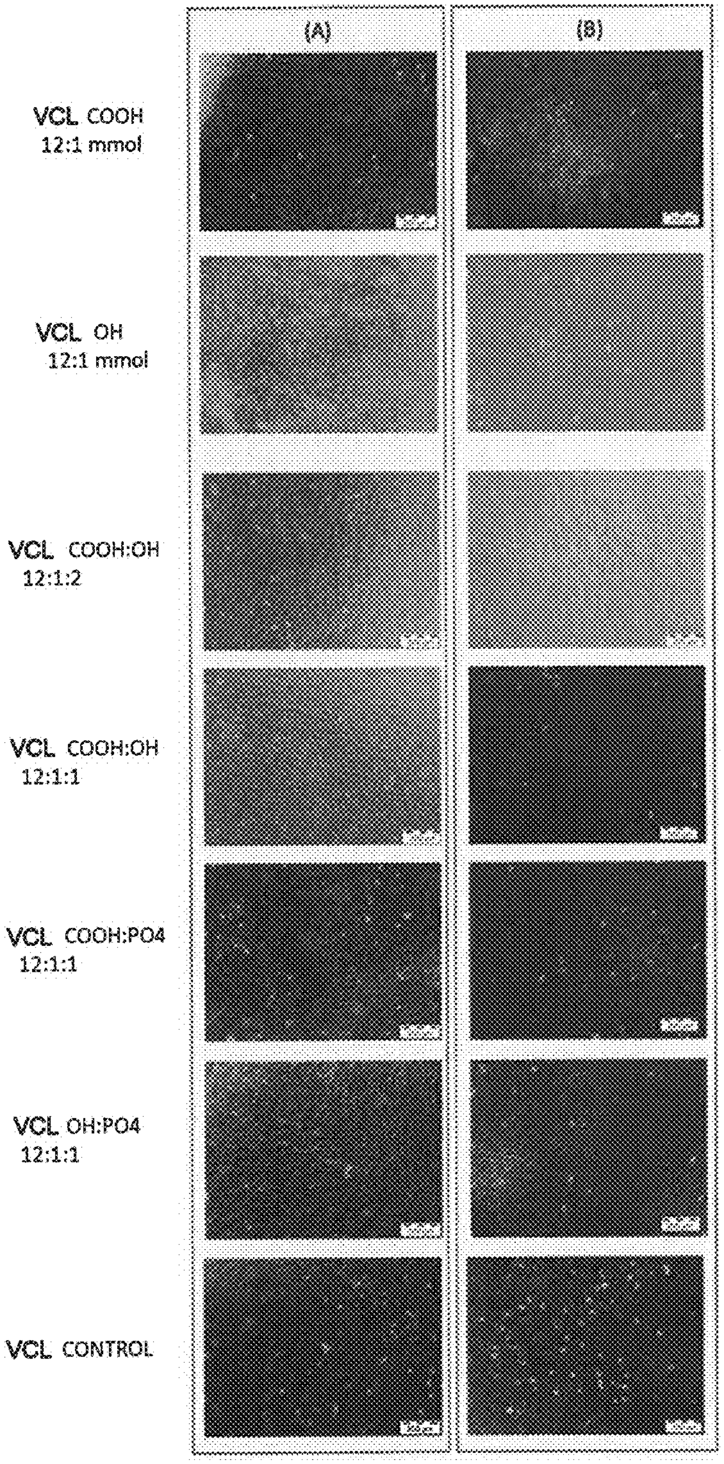
FIG. 4. A) Proliferation (**5*d*) and B) transplantation (2*d***) of MC3T3 osteoblasts from VCL hydrogels described in example 5.
Figure 5:
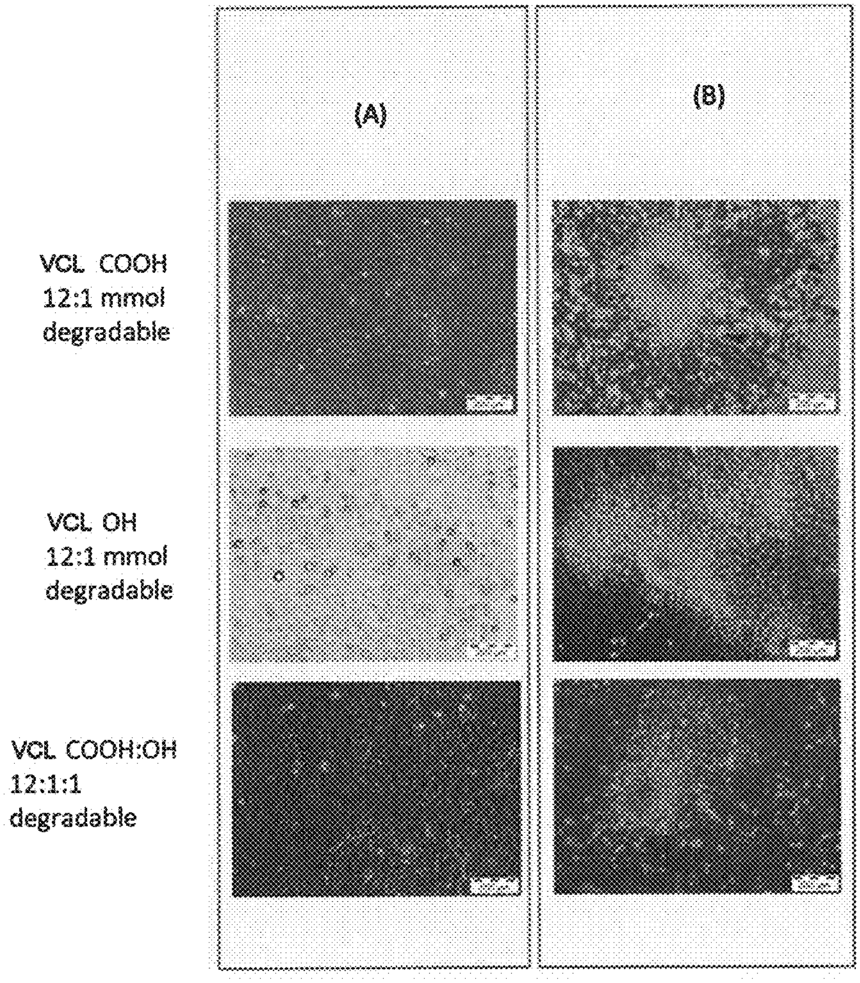
FIG. 5. A) Proliferation (**5*d*) and B) transplantation (2*d***) of MC3T3 osteoblasts from VCL resorbable hydrogels described in example 6.

By using the MC3T3 osteoblastic cell line and a culture and transplantation protocol similar to the one described, it was observed that 12:1 VCL/M-COOH and 12:1 VCL-M-OH hydrogels allow the growth and transplantation of osteoblast monolayers, being more numerous with 12:1 VCL/M-OH (FIG. 4).

The combinations analysis of 2 co-monomers showed a quite heterogeneous behavior. On the one hand, an optimal growth of osteoblast monolayers on surfaces with both M-COOH and M-OH groups was described, either in 12:1:2 or 12:1:1 ratio (FIG. 4). However, the transplantation of these monolayers was quite partial. On the other hand, 12:1 VCL/M-OH/M-$PO_4H_2$ formulation showed a superior behavior compared to the control hydrogel, with extensive monolayers and a good transplantion performance (FIG. 4).

Example 6. Preparation of Resorbable Hydrogels from VCL with Different Molar Combinations of Hydroxyethymetacrylate and Methacrylic Acid. Cell Adhesion, Proliferation and Detachment Using these Hydrogels These hydrogels were prepared in the same way as in Example 3 (according to the procedure indicated in Methods and Example 2), but using the hydrolyzable crosslinkers dC1 and dC2 (see structures and hydrogels obtained in Table 5) instead of crosslinkers C1 and C2. These crosslinkers were synthesized using routes described in the literature (*Macromolecular Bioscience* (2007), 7(4), 446-455; RSC Adv. 2014, 4, 35950-35958). After degradation, the knots in the net disappear and the hydrogel expands until the polymer chains finally dissolve. In this case, the hydrogels were evaluated in terms of cytocompatibility with the endothelial cell line C166-GFP and the osteoblastic cell line MC3T3, both to analyze the surface cell growth and its ability to detach cell monolayers by decreasing temperature. All these resorbable materials proved to be biocompatible and allowed the transplantation of monolayers to new polystyrene wells with both cell models. In some cases, as in the behavior of VCL/M-COOH/M-OH 12:1:2 with the osteoblastic line, the performance of these surfaces was even higher than their non-resorbable counterpart (FIG. 5).

TABLE 5

| | degradable 12:1 VCL/M-COOH | degradable 12:1 VCL/M-OH | degradable 12:1:2 VCL/M-COOH/M-OH |
|---|---|---|---|
| | COOH COOH | OH OH | COOH OH |
| Vinyl lactam, main component | | 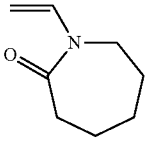 | |
| M | M-COOH 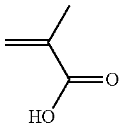 | M-COOH 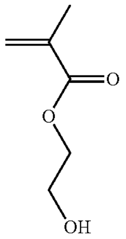 | M-COOH and M-OH 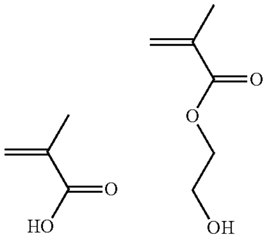 |
| VCL/M-COOH/M-OH molar ratio | 12/1/0 | 12/0/1 | 12/1/2 |
| cross-linkers structures | 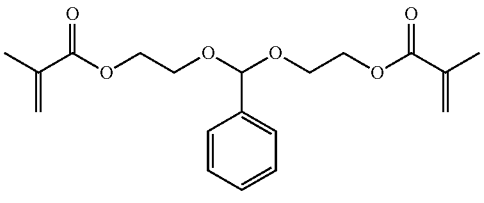 dC1 | | 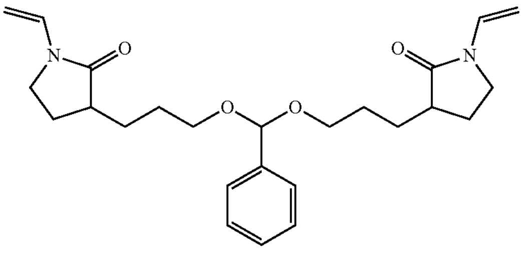 dC2 |

Example 7. Preparation of Hydrogel from VCL by Mass Polymerization. Cell Adhesion, Proliferation and Detachment Using these Hydrogels VCL-based hydrogels were prepared according to the procedure described in Example 1, but without the addition of solvent (mass polymerization). The hydrogels obtained were mechanically more robust than those obtained with solvent. They can be bent and adapted to any surface. They also proved to be superior as supports in cell culture. The hydrogels were seeded with the autofluorescent murine cell line C166-GFP, of endothelial origin, in order to evaluate the biocompatibility of the supports and their ability to detach from the culture by controlled temperature decrease. FIG. 6 shows the growth of the cell monolayer 72 h after seeding (first column of images) and the cell transplantation 72 h after temperature decrease (second column of images) for the hydrogel obtained with solvent (above) and in mass (below). All the hydrogels allowed the culture growth and its transplantation, and there were differences between them. Depending on the results obtained, a significant difference between both samples is observed, being the preparation in mass superior in adhesion and proliferation. The transplants coming from the mass prepared hydrogel are more complete and abundant.

Example 8. VCL Based Hydrogels Preparation by Thermal Initiation

VCL-based hydrogels were prepared according to the procedure described in example 1, but using 1% wt AIBN instead of HCPK, and polymerizing at 60° C. for 24 hours instead of in the photocuring chamber. Comparable hydrogels were obtained to the rest of the described examples that were obtained by photopolymerization.

The invention claimed is:

1. A hydrogel comprising:

vinyl-caprolactam type monomers, and at least two crosslinkers, wherein a first crosslinker is selected is selected from alkene(meth)acrylic (A) structures or divinylbenzene,

A

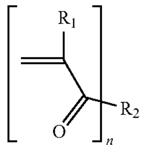

wherein:

$R_1$ is selected from hydrogen or methyl, $R_2$ is selected from di, tri, tetra or penta-substituted alkoxy, dialcoxy-disubstituted derivatives, a diaryloxy-substituted or non-substituted group, diaminoalkyl $C_1$-$C_6$ N, N' disubstituted or hexatriazine N, N', N" trisubstituted, n is selected from 2, 3, 4 or 5, and a second crosslinker is selected from the following vinyl-alkene structures, which comprise a vinyl-alkyl group or a vinyl group attached to a heteroatom (C, D)

C

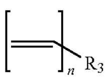

-continued

D

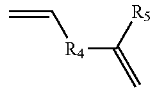

wherein:

$R_3$ is selected from dialkoxis $C_1$-$C_{12}$ disubstituted, dialkanoiloxis $C_1$-$C_{12}$ disubstituted, -imidazolin-2-one N, N'-disubstituted or 3,3'-(alkyl)-di-1-vinyl-2-lactam N, N'-disubstituted, n is selected from 2 or 3, $R_4$ is selected from an oxycarbonyl, carbonate or urea group, substituted or not with $C_1$-$C_4$ alkyl, alkoxy or alkanoloxy groups, $R_5$ is selected from hydrogen or methyl such that in the case that $R_3$ is -imidazolin-2-one N, N' disubstituted, the second crosslinker is present in a molar ratio of less than 50% with respect to the crosslinker mixture, such that in the case that it comprises an additional crosslinker, such additional crosslinker is a crosslinker that has the formula of the first crosslinker or has the formula of the second crosslinker, and excepting the hydrogel formed by vinyl-caprolactam, potassium sulfopropyl methacrylate and the crosslinkers ethylene glycol dimethacrylate and 3,3'-(propyl)-di-1-vinyl-2-pyrrolidone.

2. The hydrogel according to claim 1, wherein the first crosslinker is selected from ethylene glycol di(meth)acrylate, triethylene glycol di(meth)acrylate, tetraethylene glycol di(meth)acrylate, trimethylolpropane tri(meth)acrylate, bisphenol A di(meth)acrylate, ethoxylated bisphenol A di(meth) acrylate, pentaerythritol tri-, and tetra(meth)acrylate, tetramethylene di(meth)acrylate, N,N'-methylenebisacrylamide, divinyl benzene, polysiloxanylbisalkyl (meth)acrylate, diurethane dimethacrylate, polyethylene glycol di(meth) acrylate, and combinations thereof and the second crosslinker is selected from vinyl carbonate, triallycyanurate, methacryloxyethyl vinyl urea, dialyl itaconate, dialyl phthalate, vinylmethacrylate, divinyl adipate, divinyl pyrrolidone derivatives, 1,3-divinylimidazolin-2-one and combinations thereof.

3. The hydrogel according to claim 1, wherein each one of the crosslinkers is present in concentrations in the range 0.01-20% molar with respect to the total monomers moles.

4. The hydrogel according to claim 3, wherein the crosslinkers are ethylene glycol dimethacrylate and 1,3-divinylimidazolin-2-one.

5. The hydrogel according to claim 1, wherein the crosslinkers are ethylene glycol dimethacrylate as first crosslinker, and 3,3'-(propyl)-di-1-vinyl-2-pyrrolidone as second crosslinker.

6. The hydrogel according to claim 1, wherein at least one crosslinker is an acetal group carrier compound.

7. The hydrogel according to claim 6, wherein the first crosslinker is (((4-hydroxyphenyl)methylene)bis(oxy))bis(ethane-2,1-diyl)bis(2-methacrylate) and the second one is 3,3'-((phenylmethylene)bis(oxy))bis(propane-3,1-diyl))bis(1-vinylpyrrolidin-2-one).

8. The hydrogel according to claim 1, further comprising combinations of additional monomers.

9. The hydrogel according to claim 1, wherein the molar ratio vinyl-caprolactam/additional monomers is in the range 2/1 to 1000/1.

10. The hydrogel according to claim 1, wherein the crosslinkers are present in a percentage between 0.01% and 20% in mole of the total mole monomer content.

11. The hydrogel according to claim 1, further comprising at least one additional monomer.

12. The hydrogel according to claim 11, further comprising as additional monomers polymerizable alkene derivatives with a single polymerizable functionality.

13. The hydrogel according to claim 12, wherein the additional monomer is an alkene structure

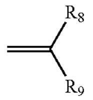

wherein $R_8$ is selected from hydrogen or methyl, $R_9$ is selected from a nitrile group, carboxylic acid, a substituted ester group, an amide group, a substituted N amide group, an amide group, N N' disubstituted, a non-substituted or substituted aryl group, an oxycarbonyl substituted group, an oxy substituted group, an amine substituted group, an amino carbonyl substituted group, a nitrogen bound N-lactam group, formamide, phosphonic, sodium sulfonate, acetamide, carbazole, imidazole, trimethylsilane and pyridine.

14. The hydrogel according to claim 12, wherein the additional monomer is selected from the following (meth) acrylic structures: hydroxyethyl(meth)acrylate, (meth) acrylic acid, potassium sulfopropylacrylate, ethylphosphate monoacrylate, oligoethylene glycol (meth)acrylates, trimethylsilyl methacrylate, polyethylene glycol (meth)acrylates, N,N dimethylacrylamide, acrylamide, alkyl (meth) acrylate, N-isopropylacrylamide, hydroxypropylmetacrylamide, N-dodecylacrylamide, N-(3-aminopropyl)methacrylamide hydrochloride, 2-aminoethyl (meth)acrylate hydrochloride, 2-(N,N-diethylamino)ethyl (meth)acrylate, N-(meth)acryloylsuccinimide, sodium 2-acrylamide-2-methyl-1-propanesulfonate, 2-acrylamide-2-methyl-1-propanesulfonic acid, [2-((meth)acryloyloxy)alkyl]trimethylammonium salts, zwitterionic sulphobetaine methacrylate, zwitterionic sulphobetaine methacrylamide, phosphorylcholine methacrylate, methacryloyl-L-lysine, carboxyethylacrylate, 2-sulfoethylmethacrylate, and combinations thereof.

15. The hydrogel according to claim 11, wherein the additional monomer is selected from maleimides, maleic acid, fumaric acid, maleates, fumarates or alkene (meth) acrylic structures.

16. The hydrogel according to claim 11, wherein the additional monomer is a styrenic structure.

17. The hydrogel according to claim 16, wherein the styrenic structure is selected from styrene, chlorostyrene, bromostyrene, vinylaniline, vinylnaphthalene, vinylbenzoate or vinylanisole.

18. The hydrogel according to claim 11, wherein the additional monomer is a vinyl structure selected from N-vinylacetamide, vinylpyrrolidone, vinylcarbazol, vinylpyridine, vinylimidazole, vinyl acetate, vinylformamide, vinylphosphonic, sodium vinylsulfonate or vinyltrimethylsilane.

19. A process to obtain a hydrogel defined in claim 1, comprising at least the following steps:

a) mixing the vinyl caprolactam monomers, one or more additional monomers, if present, solvent, if present, and at least two crosslinkers, (b) bubbling the mixture (a) with a gas, c) transfer of the product obtained in stage b) to a mold, d) polymerization, and (e) swelling of the product obtained in (d) by immersion in water or in alcohols.

20. The process according to claim 19, wherein the polymerization is carried out in a photocuring chamber and the UV radiation is maintained between 0.01 and 60 minutes.

21. The process according to claim 19, wherein the polymerization is carried out without solvent addition (step a).

22. The process according to claim 19, wherein the polymerization is carried out at a temperature between 30° C. and 120° C. for a time between 0.1 and 24 hours.

* * * * *